(12) United States Patent
Varga et al.

(10) Patent No.: US 8,607,794 B2
(45) Date of Patent: Dec. 17, 2013

(54) NON-INVASIVE BREATHING ASSISTANCE APPARATUS AND METHOD

(75) Inventors: Christopher M. Varga, Mission Viejo, CA (US); Geoffrey C. Wise, Benicia, CA (US)

(73) Assignee: CareFusion 207, Inc., San Diego, CA (US)

( * ) Notice: Subject to any disclaimer, the term of this patent is extended or adjusted under 35 U.S.C. 154(b) by 229 days.

(21) Appl. No.: 12/898,265

(22) Filed: Oct. 5, 2010

(65) Prior Publication Data
US 2012/0080033 A1   Apr. 5, 2012

(51) Int. Cl.
| A61M 16/00 | (2006.01) |
| A61M 15/08 | (2006.01) |
| A62B 7/00  | (2006.01) |
| A62B 9/00  | (2006.01) |

(52) U.S. Cl.
USPC ............. 128/204.25; 128/204.18; 128/207.18

(58) Field of Classification Search
USPC ............. 128/201.22, 201.28, 204.18, 204.25, 128/205.25, 206.21, 206.28, 207.13, 128/207.18, 911, 204.24
See application file for complete search history.

(56) References Cited

U.S. PATENT DOCUMENTS

| 4,248,218 A | 2/1981 | Fischer |
| 4,262,665 A | 4/1981 | Roalstad et al. |
| 4,274,406 A | 6/1981 | Bartholomew |
| 4,681,100 A | 7/1987 | Brychta et al. |
| 4,782,832 A | 11/1988 | Trimble et al. |
| 4,821,736 A | 4/1989 | Watson |
| 4,915,105 A | 4/1990 | Lee |
| 5,046,491 A | 9/1991 | Derrick |
| 5,113,857 A | 5/1992 | Dickerman et al. |
| 5,193,532 A | 3/1993 | Moa et al. |
| 5,231,979 A | 8/1993 | Rose et al. |
| 5,451,190 A | 9/1995 | Liardet |
| 5,477,852 A | 12/1995 | Landis et al. |
| 5,687,715 A | 11/1997 | Landis et al. |
| 5,806,516 A | 9/1998 | Beattie |
| 5,975,077 A | 11/1999 | Hofstetter et al. |
| 6,119,694 A | 9/2000 | Correa et al. |
| 6,595,215 B2 | 7/2003 | Wood |
| 6,769,432 B1 | 8/2004 | Keifer |
| 6,863,069 B2 | 3/2005 | Wood |
| 6,997,187 B2 | 2/2006 | Wood et al. |
| 7,000,613 B2 | 2/2006 | Wood et al. |
| 7,152,604 B2 | 12/2006 | Hickle et al. |

(Continued)

OTHER PUBLICATIONS

International Preliminary Report on Patentability for PCT/US2011/054787 issued Apr. 9, 2013.

*Primary Examiner* — Jackie Ho
*Assistant Examiner* — Mark K Han
(74) *Attorney, Agent, or Firm* — McDermott Will & Emery LLP

(57) ABSTRACT

An nCPAP device for assisting patient breathing includes a generator body forming an inlet, a chamber, and first and second flow circuits. The chamber directs pressurized gas from the inlet to the flow circuits. The flow circuits each include a nozzle, a channel, and at least one port. The nozzle emits a jet stream into the channel in a direction of a patient side thereof. The port fluidly connects the channel to ambient, and promotes entrainment of ambient air with the jet stream. In some embodiments, the channel forms a ramp feature directing exhaled air toward the jet stream in an angular fashion. The generator body requires reduced driving pressures to achieve target CPAP levels and reduces total imposed WOB as compared to conventional designs.

36 Claims, 13 Drawing Sheets

(56) References Cited

U.S. PATENT DOCUMENTS

| | | |
|---|---|---|
| 7,156,096 B2 | 1/2007 | Landis |
| 7,191,781 B2 | 3/2007 | Wood |
| 7,219,669 B1 | 5/2007 | Lovell et al. |
| 7,353,826 B2 | 4/2008 | Sleeper et al. |
| 7,578,294 B2 | 8/2009 | Pierro et al. |
| 2002/0053347 A1 | 5/2002 | Ziaee |
| 2003/0000527 A1 | 1/2003 | Stenzler et al. |
| 2003/0047185 A1 | 3/2003 | Olsen et al. |
| 2003/0079749 A1 | 5/2003 | Strickland et al. |
| 2003/0200970 A1 | 10/2003 | Stenzler et al. |
| 2004/0065330 A1 | 4/2004 | Landis |
| 2004/0244804 A1 | 12/2004 | Olsen et al. |
| 2005/0011524 A1 | 1/2005 | Thomlinson et al. |
| 2005/0133039 A1 | 6/2005 | Wood |
| 2005/0199242 A1 | 9/2005 | Matula, Jr. et al. |
| 2005/0241644 A1 | 11/2005 | Gunaratnam et al. |
| 2006/0042631 A1 | 3/2006 | Martin et al. |
| 2006/0042634 A1 | 3/2006 | Nalagatla et al. |
| 2006/0130840 A1 | 6/2006 | Porat et al. |
| 2006/0174887 A1 | 8/2006 | Chandran et al. |
| 2006/0180149 A1 | 8/2006 | Matarasso |
| 2006/0231103 A1 | 10/2006 | Matula, Jr. et al. |
| 2006/0266361 A1 | 11/2006 | Hernandez |
| 2007/0074724 A1 * | 4/2007 | Duquette et al. .......... 128/204.18 |
| 2007/0125379 A1 | 6/2007 | Pierro et al. |
| 2007/0125384 A1 | 6/2007 | Zollinger et al. |
| 2007/0125387 A1 | 6/2007 | Zollinger et al. |
| 2007/0163600 A1 | 7/2007 | Hoffman |
| 2007/0175473 A1 | 8/2007 | Lewis et al. |
| 2007/0186930 A1 | 8/2007 | Davidson et al. |
| 2007/0246043 A1 | 10/2007 | Kwok et al. |
| 2008/0295846 A1 * | 12/2008 | Han et al. ................. 128/207.13 |
| 2009/0165799 A1 | 7/2009 | Duquette et al. |
| 2010/0108073 A1 | 5/2010 | Zollinger et al. |
| 2010/0252044 A1 | 10/2010 | Duquette et al. |

\* cited by examiner

NON-INVASIVE BREATHING ASSISTANCE APPARATUS AND METHOD

BACKGROUND

The present disclosure generally relates to devices and methods for generating and delivering continuous positive airway pressure therapy or other non-invasive breathing assistance to patients, such as infants. More particularly, the present disclosure relates to variable flow, nasal continuous positive airway pressure systems, devices, and methods with reduced driving pressure requirements and improved work-of-breathing.

Continuous positive airway pressure (CPAP) therapy has been employed for many years to treat patients experiencing respiratory difficulties and/or insufficiencies. In addition, CPAP therapy can beneficially assist patients with underdeveloped lungs (in particular, infants and especially premature infants or neonates) by preventing lung collapse during exhalation and assisting lung expansion during inhalation.

In general terms, CPAP therapy entails the continuous transmission of positive pressure into the lungs of a spontaneously breathing patient throughout the respiratory cycle. CPAP can be delivered to the patient using a variety of patient interface devices, for example an endotracheal tube or nasal cannula. With infants, however, it is more desirable to employ a non-invasive patient interface device, in particular one that interfaces directly or indirectly with the nasal airways via the patient's nares. Such systems are commonly referred as nasal continuous positive airway pressure (nCPAP) systems.

In theory, the CPAP system should deliver a constant, stable pressure (above atmospheric pressure) to the patient's airways. With conventional CPAP systems, a relatively constant and continuous flow of gas (e.g., air, oxygen, etc.) is delivered into the patient's airways, with this airflow creating a pressure within the patient's lungs via a restriction placed on outflow from the patient. Unfortunately, this continuous flow can have an adverse effect on the patient's respiratory synchrony. More particularly, the patient is required to exhale against the incoming gas, thus increasing the patient's work-of-breathing. Control valves can be employed to better accommodate inspiratory and expiratory stages of a patient's breathing cycle (e.g., controlling gas flow into the system and/or altering an extent of restriction from outflow from the system). However, for many patients, especially infants, this approach is less than satisfactory as the patient's required work-of-breathing is quite high. That is to say, it is essentially impossible for a control valve system to accurately replicate the actual respiratory cycles experienced by the patient, such that the patient will consistently be required to exhale against the momentum of the incoming gas, as well as against the resistance of the control valve(s). For an infant with underdeveloped lungs, even a slight increase in the required work-of-breathing may render the CPAP system in question impractical.

More recently, nCPAP systems have been developed that incorporate a variable flow concept in combination with separate channels for inspiratory and expiratory gas to and from the patient. When the patient inhales, the incoming gas takes the path of least resistance and is directed to the patient's airways. Upon expiration, the gas again takes the path of least resistance and goes out an exhaust port, thus reducing resistance during the expiratory phase of breathing. For example, the Infant Flow™ system, available from CareFusion, Inc., of San Diego, Calif., includes a variable flow CPAP generating device (or "CPAP generator") that causes the direction of the supply gas to change with the infant's breathing patterns while maintaining a nearly constant pressure throughout the respiratory cycle. The Infant Flow CPAP generator converts supplied gas into jet streams (one for each naris), with the momentum of the gas jet creating a positive pressure inside the patient's lungs, in accordance with known physics principles. To accommodate expiratory flow from the patient, the Infant Flow CPAP generator relies upon what the manufacturer's literature lists as a "fluidic flip" effect. The expiratory airflow from the patient applies a pressure onto the incoming jet steam flow. It has been theorized that due to the Coanda effect, the expiratory airflow causes the jet stream flow to deflect, thus triggering a fluidic flip of the incoming jet flow. As a result, the jet stream and the expiratory airflow readily proceed to the exhaust port, thus reducing the patient's required work-of-breathing. While quite promising, the jet streams generated in such devices have a relatively high momentum that may not be easily overcome by the patient's expiratory breathing, especially with infants. Moreover, driving gas pressure levels that must be applied to these and other commercially available variable-flow CPAP generators to produce therapeutic CPAP levels are not sufficiently low to permit usage with a common ventilator. Instead, a dedicated high-pressure flow driver is required.

In light of the above, needs exist for improved nCPAP systems, devices, and methods.

SUMMARY

Some aspects in accordance with principles of the present disclosure relate to a nasal continuous positive airway pressure (nCPAP) device for assisting patient breathing. The device includes a generator body forming an inlet, a chamber, and first and second flow circuits. The inlet is configured for fluid connection to a source of pressurized gas. The chamber is fluidly connected to the inlet. The first and second flow circuits are fluidly connected to the chamber and each include a nozzle, a channel, and an open port. The nozzle defines an inlet end and an outlet end, with the inlet end being fluidly connected to the chamber. The outlet end is opposite the inlet end, has a diameter less than the diameter of the inlet end, and is adapted to emit a gas jet stream into the channel. The channel has or defines a nozzle side fluidly connected to the outlet end of the nozzle, and a naris or patient side opposite the nozzle side for interfacing with a patient's naris. Each of the channels forms a ramp feature having an inclined region extending from a location of the open port in a direction of the patient side, and a declined region extending from the inclined region toward the patient side. In some embodiments, the ramp feature promotes jet stream flow patterns that rapidly switch from inside the channel to the open port. For example, the declined region facilitates diversion of the jet stream by exhaled airflow during the expiratory phase of operation, and the inclined region optionally facilitates return of the jet stream into the channel during the inspiratory phase of operation. The port is open to ambient, and is fluidly connected to the channel at a location between the nozzle side and the patient side. During use, pressurized gas delivered to the chamber via the inlet is converted to a fixed flow jet stream by the nozzles, creating CPAP in each of the channels. Further, the generator body establishes an inspiratory flow pattern during an inspiratory stage of breathing and an expiratory flow pattern during an expiratory stage of breathing. With the expiratory flow pattern, exhaled air from the patient side of each of the channels is directed by the ramp feature to cause at least a portion of the jet stream flow to divert to, and exhaust from, the corresponding port. The generator bodies of the present disclosure require reduced inlet or driving pressures to achieve desired therapeutic CPAP levels and/or reduce total imposed work-of-breathing by the patient.

Other aspects in accordance with principles of the present disclosure relate to a nasal continuous positive airway pressure (nCPAP) system including a generator body, a patient interface piece, and a source of gas. The generator body defines an inlet, a chamber, and first and second flow circuits. The chamber is fluidly connected to the inlet, and the flow circuits are fluidly connected to the chamber. Each of the flow circuits includes a nozzle, a channel, and a port. The nozzle creates a jet stream from pressurized gas in the chamber, and directs the jet stream into a nozzle side of the channel. The port is open to ambient and is fluidly connected to the channel at a location between the nozzle side and an opposite, patient side of the channel. The patient interface includes first and second prongs fluidly connected to the patient side of the channels, respectively, and is configured for fluid connection to a patient's nares. Finally, the source of gas is fluidly connected to the inlet of the generator body and provides a continuous flow of pressurized gas. Upon connection of the interface piece to the patient's nares and of the source of gas to the inlet, a fixed amount of jet stream flow is established in each of the channels by the corresponding nozzle. Momentum of the jet streams deliver CPAP to the patient. In an inspiratory phase of operation, ambient air is, where necessary, entrained into the jet stream flow delivered to the patient's nares via the corresponding ports. In an expiratory phase, exhaled air from the patient nares diverts the jet stream flow from the nozzle and is exhausted through the corresponding ports. In some embodiments, the system is configured to provide a CPAP level of 5 cm $H_2O$ and total imposed work-of-breathing of not greater than 140 mJ/L for a 9 mL tidal volume patient under conditions where the source of gas is delivering a driving pressure of not more than 25 cm $H_2O$. At these lower pressure operating conditions, the source of gas can be a common ventilator.

Yet other aspects in accordance with principles of the present disclosure relate to a method for establishing and delivering a continuous positive airway pressure to a patient. The method includes fluidly connecting a generator body to nares of the patient. The generator body forms first and second flow circuits each including a nozzle, a channel, and a port. The channel includes first and second ramp regions. The port fluidly connects the channel with ambient air at a location between an outlet end of the nozzle and a patient side of the channel. Gas from a source of pressurized gas is forced at a driving pressure to an inlet end of each of the nozzles. A jet stream from each of the nozzles is directed toward the patient's nares via the channel to establish a continuous positive airway pressure in the patient's airway. During periods of patient exhalation, exhaled air from is directed by the second ramp region to divert the jet stream to the port at which the jet stream is exhausted from the generator body. In some embodiments, the driving pressure is not greater than 110 cm $H_2O$ and the established continuous positive airway pressure level is 20 cm $H_2O$. In some other embodiments, the driving pressure is not greater than 25 cm $H_2O$, the established continuous positive airway pressure is 5 cm $H_2O$, and a total imposed work-of-breathing for a 24 mL tidal volume patient during the periods of inhalation and exhalation is not greater than 200 mJ/L.

DETAILED DESCRIPTION

Figure 1:
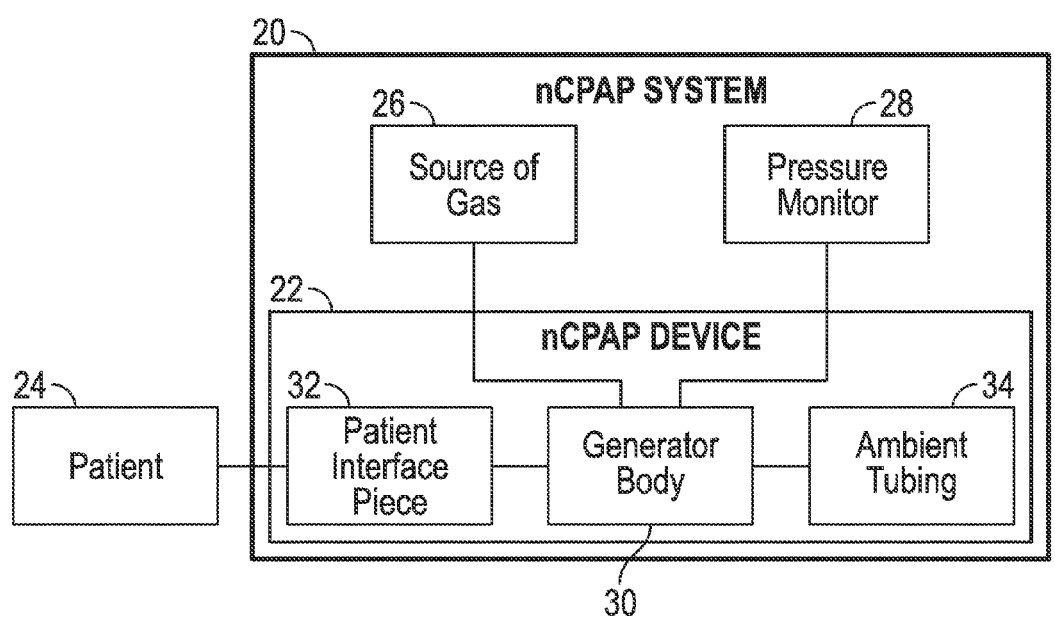
FIG. 1 is a block diagram illustrating one embodiment of a nasal continuous positive airway pressure system including an nCPAP device in accordance with principles of the present disclosure.

One embodiment of a nasal continuous positive airway pressure (nCPAP) system 20 incorporating an nCPAP device 22 in accordance with principles of the present disclosure is shown in block form in FIG. 1. In general terms, the system 20 is adapted to provide CPAP therapy to a patient 24, and includes the nCPAP device 22 and a source of pressurized gas 26. The nCPAP system 20 can further optionally include a pressure monitor 28. The nCPAP device 22 is described in greater detail below, and generally includes a generator body 30 and a patient interface piece 32. Optionally, ambient air tubing 34 can also be provided. The generator body 30 is fluidly connected to the patient interface 32 and the optional ambient air tubing 34, with the patient interface piece 32 being adapted to establish fluid communication with the patient's 24 nasal airways. The source of pressurized gas 26 provides the generator body 30 with a continuous flow of gas (e.g., air and/or oxygen). Where provided, the pressure monitor 28 is also fluidly connected to the generator body 30 and samples or measures pressure therein. During use, the generator body 30 acts upon gas from the source 26 to generate and deliver a continuous positive airway pressure to the patient 24 via the patient interface piece 32. As the patient 24 exhales, the exhaled air readily flows through the patient interface piece 32/generator body 30, and is exhausted from the nCPAP device 22 as described below.

Figure 2A:
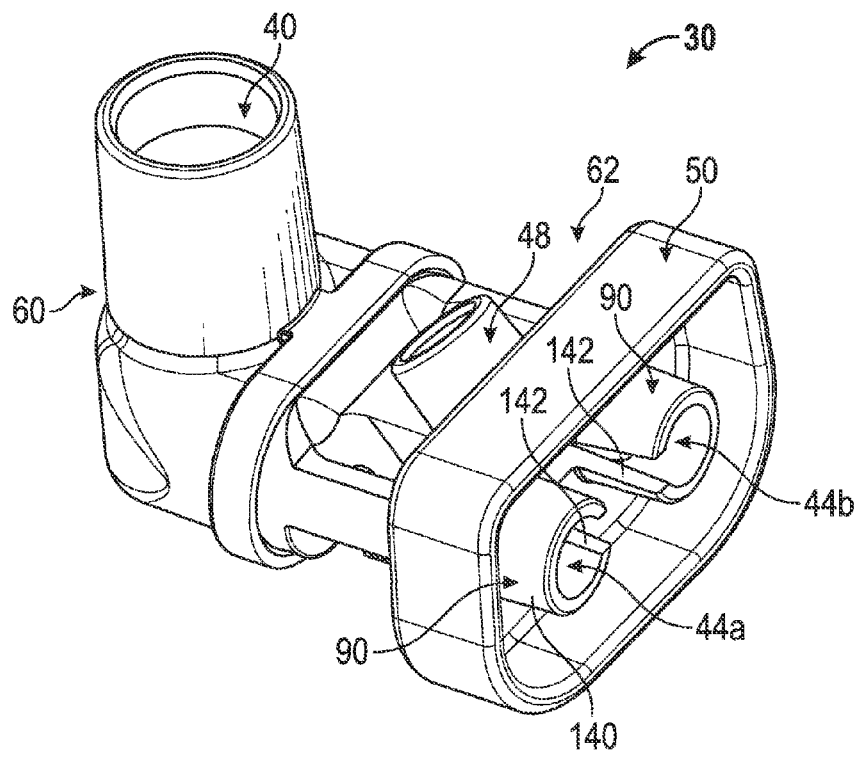
FIG. 2A is a perspective view of a generator body in accordance with principles of the present disclosure and useful with the nCPAP device of FIG. 1.
Figure 2B:
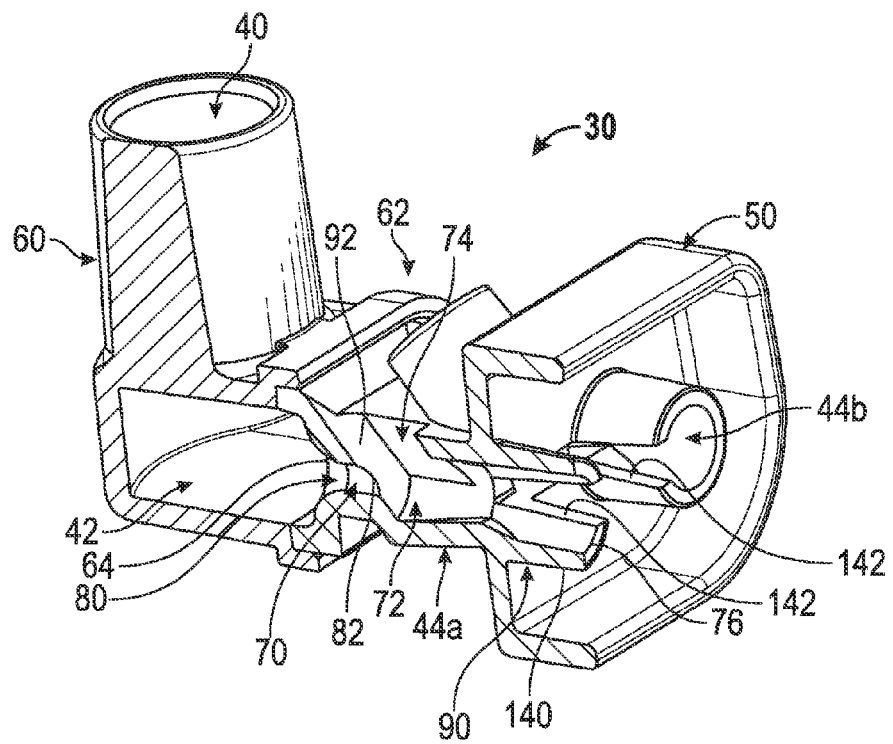
FIG. 2B is a perspective cross-sectional view of the generator body of FIG. 2A.

One embodiment of the generator body 30 in accordance with principles of the present disclosure is shown in FIGS. 2A and 2B. In general terms, the generator body 30 is configured to establish CPAP for inspiratory and expiratory flow of gas to and from the patient 24 (FIG. 1). With this in mind, the generator body 30 forms or defines a supply gas inlet 40, a chamber 42 (shown in FIG. 2B), and first and second flow circuits 44a, 44b (referenced generally in FIG. 2A; the first flow circuit 44a being shown in greater detail in FIG. 2B). In general terms, the inlet 40 is configured for fluid connection to the source of pressurized gas 26 (FIG. 1), and directs incoming gas into the chamber 42. The flow circuits 44a, 44b are fluidly connected to the chamber 42. Thus, gas flow provided at the inlet 40 is directed through the chamber 42 and then toward the patient via the flow circuits 44a, 44b. In this regard, and as described in greater detail below, the flow circuits 44a, 44b incorporate one or more features that promote exhausting of supplied gas and exhaled air during inspiratory and expiratory phases of operation with minimal patient work-of-breathing effort. The generator body 30 can incorporate additional, optional components, such as a pressure monitoring port 48, an exterior flange 50, etc.

In some embodiments, the generator body 30 can have a two (or more) piece construction, including a supply section 60 and a circuit section 62. The sections 60, 62 can be separately formed (e.g., molded plastic) and assembled to another, with the supply section 60 forming the inlet 40 and the chamber 42. The circuit section 62 forms the flow circuits 44a, 44b. Alternatively, other constructions are also envisioned, such as integrally constructing the generator body 30 as a single, homogenous body.

The inlet 40 can assume various forms (e.g., size and shape) appropriate for fluid connection to a supply tube (not shown) extending from the source of gas 26 (FIG. 1). As best shown in FIG. 2B, the chamber 42 is fluidly connected to the supply inlet 40 and is fluidly open to the first and second flow circuits 44a, 44b, with FIG. 2B illustrating fluid communication between the chamber 42 and the first flow circuit 44a. Effectively, then, an internal wall 64 (referenced generally in FIG. 2B) provides or forms a manifold that is fluidly open to the chamber 42 and the flow circuits 44a, 44b.

The first and second flow circuits 44a, 44b are, in some embodiments, identical such that the following description of the first flow circuit 44a is equally applicable to the second flow circuit 44b. The first flow circuit 44a includes or defines a nozzle 70, a channel 72, and at least one open port 74. The nozzle 70 is fluidly open to the channel 72, as is the open port(s) 74. As described in greater detail below, then, gas flow from the nozzle 70 is forced into the channel 72 in a direction of a naris or patient side 76 of the channel 72. During patient inhalation, ambient air can be entrained into the delivered gas flow and/or excess gas exhausted via the port 74 depending upon the patient's inspiratory requirements. Conversely, exhaled air from the patient at the patient side 76 can be exhausted through the open port(s) 74, as can diverted jet stream flow from the nozzle 70.

The nozzle 70 can assume various forms, and generally includes or defines an inlet end 80 and an outlet end 82. The inlet end 80 is fluidly connected to the chamber 42. The outlet end 82 is opposite the inlet end 80, and is positioned to direct gas flow into the channel 72. The outlet end 82 has a reduced diameter as compared to the inlet end 80. With this construction, pressurized gas in the chamber 42 (via the inlet 40) is forced to the nozzle 70, that in turn converts the gas flow into a low momentum jet stream directed into the channel 72. The so-generated jet stream is described in greater detail below. Generally, however, the jet stream acts within the channel 72, generally directed toward the patient side 76 (and thus the patient) to create a continuous positive airway pressure (e.g., the jet stream momentum is converted into pressure).

The channel 72 is generally defined by a tube-like body 90 extending from the patient side 76 to a nozzle side 92 that is fluidly connected to the outlet end 82 of the nozzle 70. The open port 74 is formed through a thickness of a wall of the tubular body 90, and thus is fluidly open to the channel 72. A geometry of the channel 72 in extension from the open port 74 to the patient side 76 establishes desired gas flow patterns during the inspiratory and expiratory phases of operation as described below.

Figure 2C:
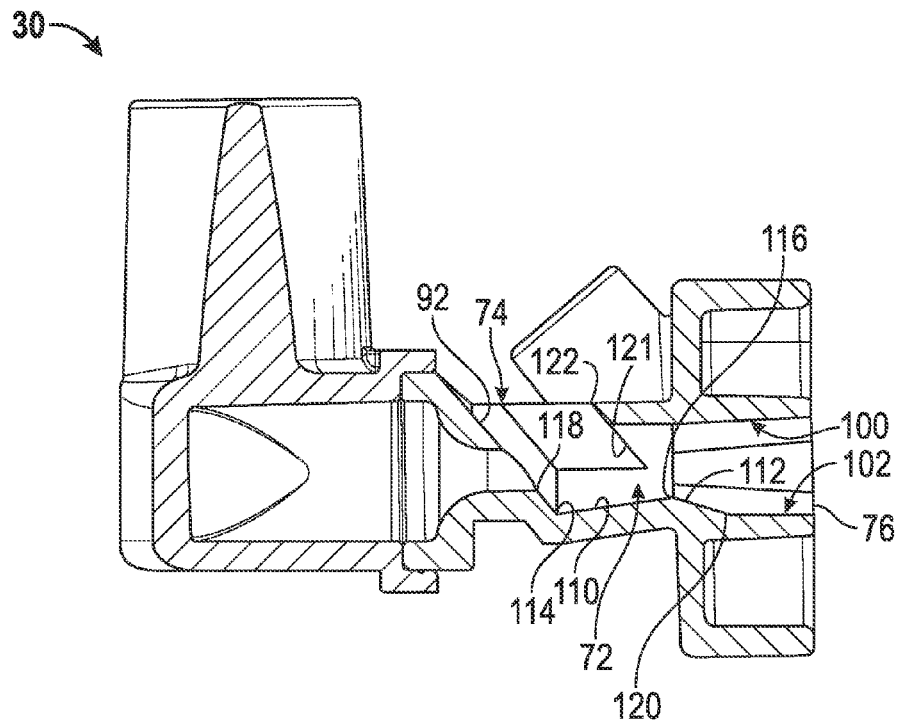
FIG. 2C is a longitudinal cross-sectional view of the generator body of FIG. 2A.

In particular, relative to the cross-sectional view of FIG. 2C, the channel 72 can be described as having or being defined by an upper wall surface 100 and a lower wall surface 102. The open port 74 is fluidly open to the channel 72 at the upper wall surface 100. The lower wall surface 102 is defined opposite the upper wall surface 100 and includes first and second ramp regions 110, 112. The first ramp region 110 extends from a port location 114 (otherwise aligned with the open port 74) to a transition location or peak 116 that is longitudinally displaced from the open port 74 in a direction of the patient side 76. As a point of reference, the channel 72 can have an increased or elevated diameter at the port location 114, for example by forming an angled guide surface 118 at the nozzle side 92 (e.g., the angled guide surface 118 can be arranged at an angle on the order of 40 degree from vertical in some embodiments). Regardless, the first ramp region 110 has an inclined or ascending orientation relative to the upper wall surface 100 in extension from the port location 114 to the transition location 116. Stated otherwise, a linear distance between a plane (relative to the longitudinal cross-sectional view of FIG. 2C) of the upper wall surface 100 and the lower wall surface 102 at the port location 114 is greater than a linear distance between the upper wall surface 100 and the lower wall surface 102 at the transition location 116.

The second ramp region 112 extends from the transition location 116 to or toward the patient side 76. For example, the second ramp region 112 can be characterized as terminating at an intermediate location 120 that is spatially between the patient side 76 and the transition location 116. The second ramp region 112 has a declined or descending arrangement relative to the upper wall surface 100 in extension from the transition location 116 to the intermediate location 120. Stated otherwise, a linear distance between the upper wall surface 100 and the lower wall surface 102 at the transition location 116 is less than a linear distance between the upper wall surface 100 and the lower wall surface 102 at the intermediate location 120. In some embodiments, the descending orientation or arrangement of the second ramp region 112 can continue to the patient side 76. With the one embodiment of FIG. 2C, however, the channel 72 has a relatively uniform diameter in extension from the intermediate location 120 to the patient side 76.

A slope of the first ramp region 110 can be less than a slope of the second ramp region 112 as shown. Alternatively, other slope relationships are also envisioned. Regardless, the ramp regions 110, 112 serve as flow directors relative to gas flow to and from the patient side 76 as described below.

Figure 3:
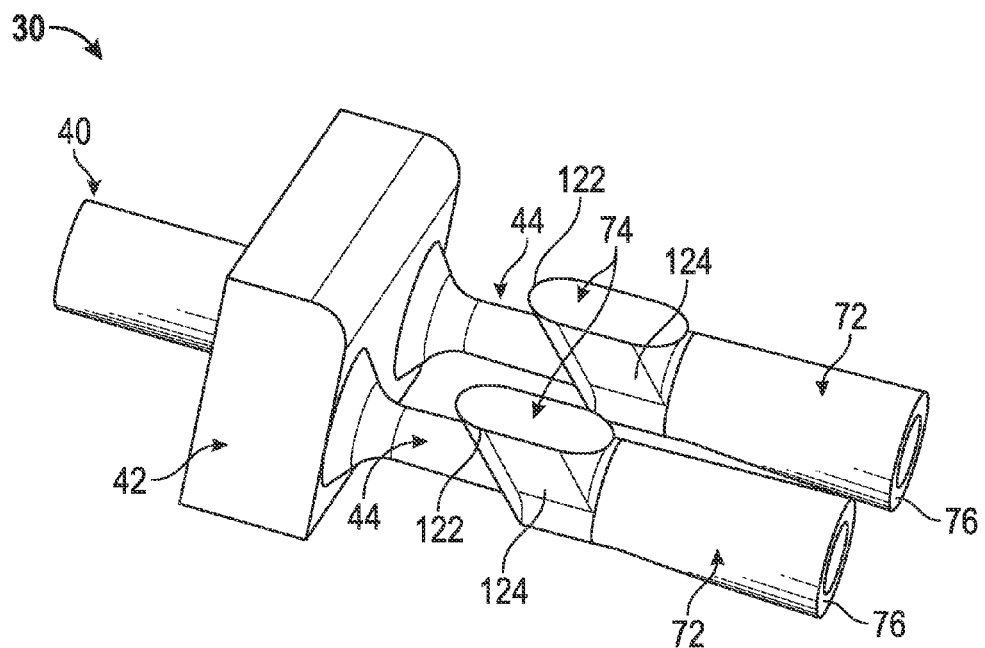
FIG. 3 is a perspective modeling of an internal fluid volume of the generator body of FIG. 2A.

The open port 74 is open to the channel 72 at an interior aperture 121 in the upper wall surface 100, and is open to ambient at an exterior aperture 122. The port 74 can have an expanding cross-sectional area in extension from the interior aperture 121 to the exterior aperture 122. In some embodiments, and as reflected by the internal fluid volume model of the generator body of FIG. 3, opposing side walls 124 (theoretically represented in FIG. 3) of the port 74 can have an angular extension to the exterior aperture 122, further contributing to the expanding cross-sectional area construction of the port 74. Regardless, the open port 74 can be referred to as an ambient port, serving to fluidly connect the channel 72 with ambient air/pressure. It will be understood, however, that an intermediate body or device (e.g., exhaust tubing, return line, etc.), can be assembled to the open port 74 in establishing an ambient-type connection. While the generator body 30 is shown as including the single port 74 with each of the flow circuits 44, in other embodiments, one or more secondary ports can be provided as described below.

Figure 4A:
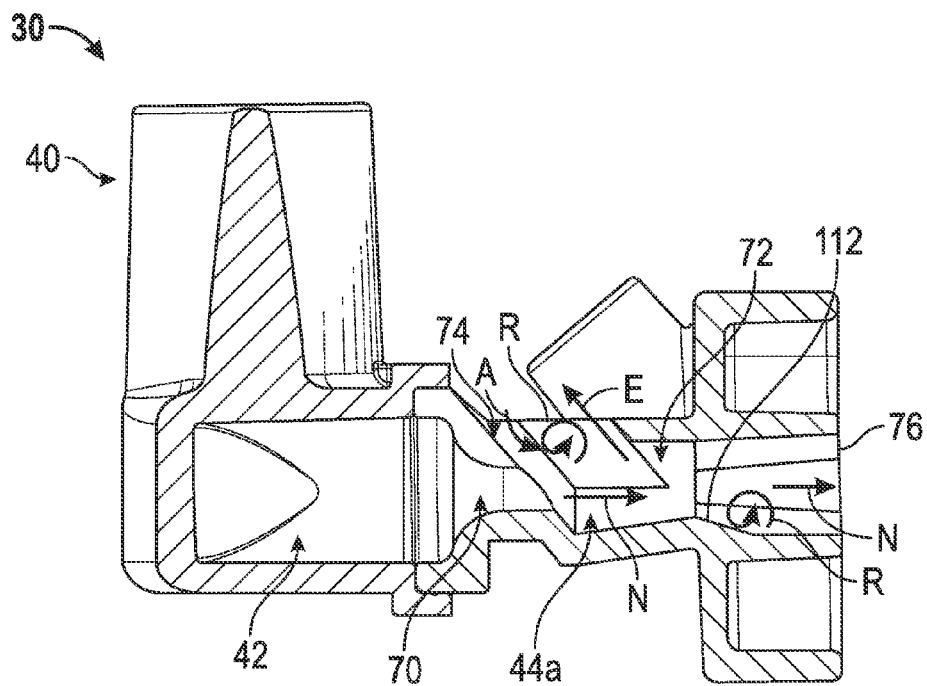
FIG. 4A is a cross-sectional view of the generator body of FIG. 2A and illustrating fluid flow during an inspiratory phase of operation.

During operation, pressurized gas (e.g., from the source of gas 26 (FIG. 1)) is provided to the chamber 42 via the supply inlet 40. The supplied gas is forced into the flow circuits 44. As shown for the first flow circuit 44a in FIG. 4A, the nozzle 70 converts the gas flow to a jet stream N that is directed into the channel 72. As a point of reference, FIG. 4A illustrates the generator body 30 during an inspiratory stage of operation. Pressurized gas is delivered to the chamber 42 via the supply inlet 40 and is directed toward the flow circuits 44. With respect to the first flow circuit 44a shown, the nozzle 70 converts the delivered gas into a jet stream (represented by arrows N in FIG. 4A) that is directed to the channel 72. The jet stream N establishes a continuous positive airway pressure within the channel 72 (i.e., the jet stream N momentum is converted into pressure) that is applied to the patient side 76, and thus the patient. At least a portion of the jet stream N flow is directed through the channel 72 and delivered to/inhaled by the patient at the patient side 76. Depending upon the patient's inspiratory requirements, ambient air (represented by arrows A in FIG. 4A) can be entrained into the delivered jet stream N via the open port 74. Similarly, and as a function of the patient's respiratory needs, a portion of the jet stream N experiences a recirculating flow R adjacent the open port 74 as well as along the second ramp region 112. These recirculating flows R, in turn, divert an excess portion (represented by arrow E in FIG. 4A) of the jet stream N and/or entrained air A to the open port 74 as exhaust flow. Thus, when the jet stream N flow exceeds the inspiratory demand of the patient, excess gas is exhausted via the port 74.

Figure 4B:
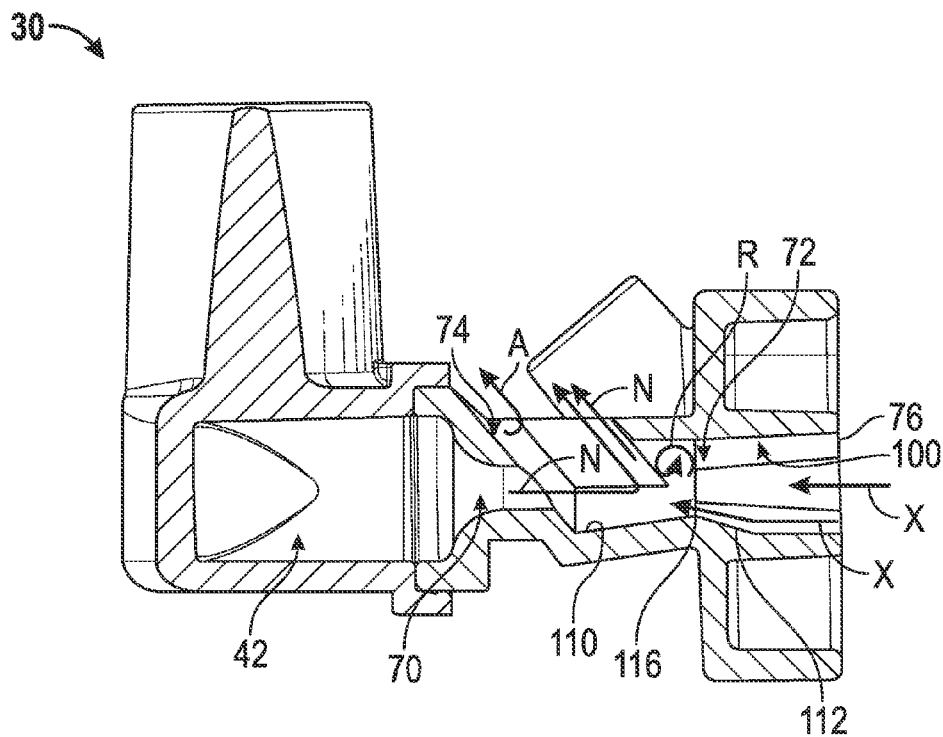
FIG. 4B is a cross-sectional view of the generator body of FIG. 2A and illustrating fluid flow during an expiratory phase of operation.

During the expiratory phase of operation shown in FIG. 4B, the jet stream N continues to be generated by and emitted from the nozzle 70 into the channel 72, maintaining the continuous positive airway pressure delivered to the patient due to the jet stream's momentum. Exhaled air (represented by arrows X in FIG. 4B) enters the channel 72 at the patient side 76, and acts upon the jet stream N flow. In this regard, relative to a flow direction of the exhaled air X, the second ramp region 112 defines a tapering hydraulic diameter that increases the magnitude of the velocity of the exhaled air X at the transition location or peak 116. Further, the second ramp region 112 effectively "focuses" a portion of the exhaled air X "upwardly" toward the jet stream N flow. This focused, upward flow diverts or "turns" the jet stream N (and any entrained ambient air A) toward the open port 74. Also, a recirculating flow (represented by arrow R in FIG. 4B) is formed between the jet stream N and the exhaled air X adjacent the upper wall surface 100 in a zone of the first ramp region 110 that enhances diversion of the jet stream N toward the open port 74. The jet stream N, as well as a substantial portion of the exhaled air X and any ambient air A, exhausts from the generator body 30 via the open port 74. Thus, the open port 74 the ramp regions 110, 112, and a geometry of the jet stream N combine to establish flow patterns that minimize resistance to the exhaled air X and patient effort required to draw the jet stream N back into the channel 72 upon inspiration. This results in low patient work-of-breathing during both inspiratory and expiratory operation.

It has surprisingly been found that the ramp features described above in combination with one or more geometry characteristics render the generator body 30 capable of establishing desired CPAP levels at low driving pressures and with minimal patient work-of-breathing. For example, in some embodiments, the nozzle outlet end 82 has a diameter (and thus a diameter of the resultant jet stream N) on the order of 0.04-0.07 inch, optionally 0.058 inch. A diameter (or height) of the channel 72 at the patient side 76 is on the order of 0.10-0.16 inch, optionally 0.136 inch. With these and other geometry considerations, the generator body 30 optionally establishes a ratio of channel height (at the patient side 76) to jet diameter in the range of 2.29-2.50, optionally 2.34. An angle of incline (relative to horizontal) along the first ramp region 110 is in the range of 5°-10°, optionally 7.1°; an angle of decline (relative to horizontal) along the second ramp region 112 is in the range of 12°-19°, optionally 16.5°.

Returning to FIGS. 2A and 2B, the optional pressure monitoring port 48 is located to tap or sample air pressure within the generator body 30. The pressure monitoring port 48 can be fluidly connected to one or both of the flow circuits 44a, 44b, and provides a surface appropriate for connection to monitoring tubing (not shown) extending to the pressure monitor 28 (FIG. 1). In other embodiments, the pressure monitoring port 48 can be omitted.

The optional exterior flange 50 surrounds the tube bodies 90, and serves to direct or deflect exhausted airflow away from the patient. In other embodiments, the exterior flange 50 provides a surface for mounting of various other components, such as the patient interface 32 described below. In other embodiments, the flange 50 can be omitted.

As best shown in FIGS. 2A and 2B, the generator body 30 can incorporate additional features facilitating connection with other components of the nCPAP system 20 (FIG. 1) and/or desired functioning. For example, the tube bodies 90 associated with the flow circuits 44a, 44b can form or define an exterior taper 140 adapted to promote a secured, sealed attachment with the patient interface piece 32 (FIG. 1), along with radial slots 142 that provide a region from which pressure otherwise present in the corresponding channel 72 can be tapped or sampled.

Figure 5:
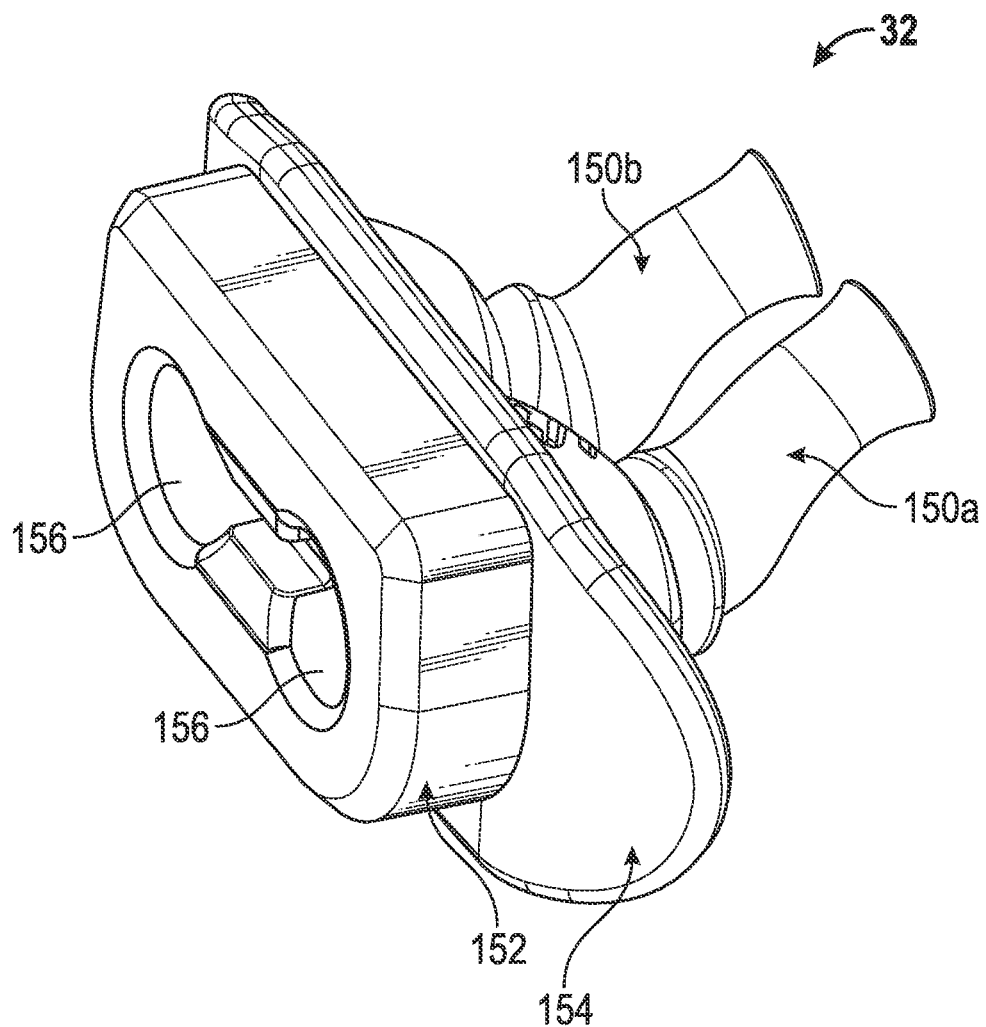
FIG. 5 is a perspective view of a patient interface piece useful with the system of FIG. 1.

Returning to FIG. 1, the patient interface 32 useful with the generator bodies of the present disclosure can assume various forms. For example, FIG. 5 generally illustrates one exemplary embodiment of the patient interface piece 32 that includes a pair of nasal prongs 150a, 150b projecting from a base 152. The base 152 can incorporate additional features, such as a sealing flange 154. With reference between FIGS. 2A and 5, the base 152 is generally sized and shaped for assembly to the generator body 30, for example via a perimeter shape including a shape of the flange 50. The base 152 forms a pair of apertures 156 sized to be received over respective ones of the fluid circuit tubular bodies 90. The nasal prongs 150a, 150b may be of any size and shape as are suitable for interacting with the patient's nares, and are fluidly open to the apertures 156. Assembly of the patient interface piece 32 to the generator body 30 generally entails establishing a fluid connection between the nasal prongs 150a, 150b, and the patient side 76 of a respective one of the flow circuits 44a, 44b. In other embodiments, the patient interface 32 can be a nasal mask.

Figure 6A:
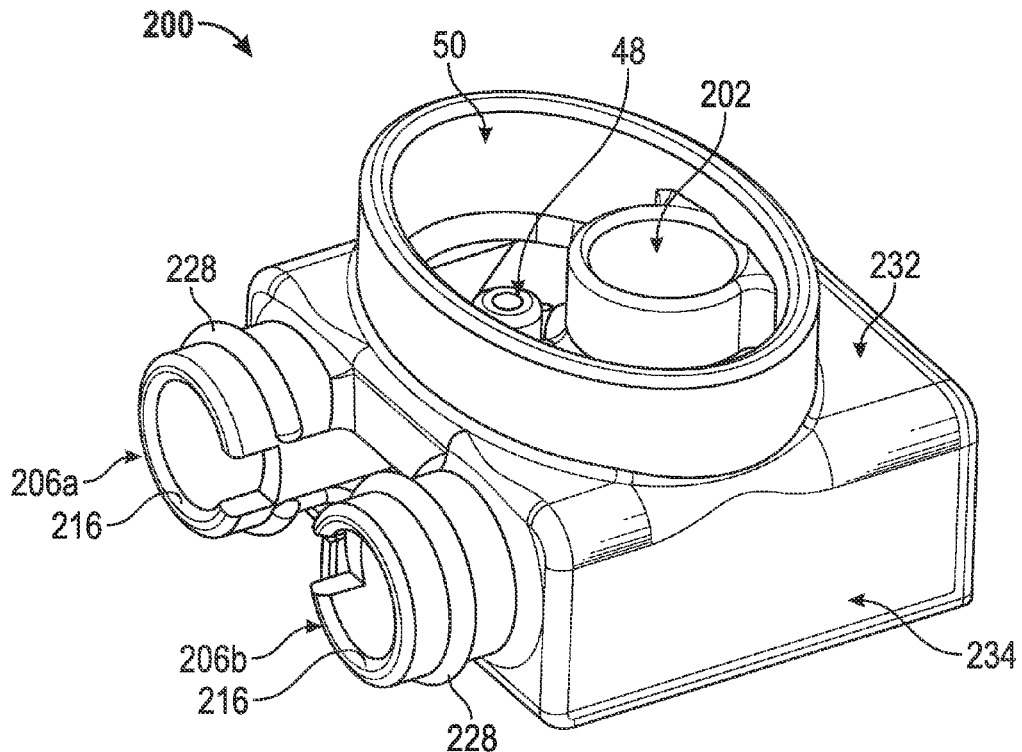
FIG. 6A is a perspective view of another generator body in accordance with principles of the present disclosure and useful with the nCPAP device of FIG. 1.
Figure 6B:
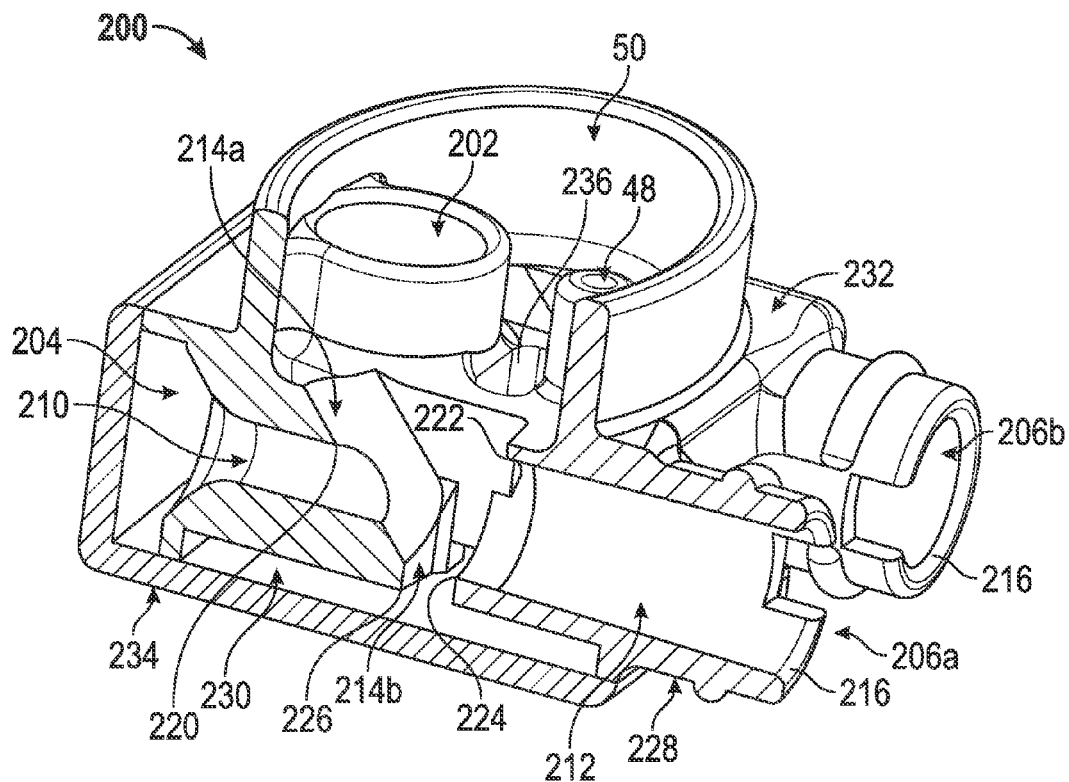
FIG. 6B is a perspective cross-sectional view of the generator body of FIG. 6A.

Another generator body 200 in accordance with principles of the present disclosure and useful with the nCPAP system 20 (FIG. 1) is shown in FIGS. 6A and 6B. As with the generator body 30, the generator body 200 forms or defines a gas supply inlet 202, a chamber 204, and first and second flow circuits 206a, 206b (one of which is more clearly visible in the view of FIG. 6B). The supply inlet 202 and the chamber 204 are akin to the inlet 40 (FIG. 2A) and the chamber 42 (FIG. 2B) described above, with the chamber 204 fluidly connecting the supply inlet 202 with the flow circuits 206a, 206b. The flow circuits 206a, 206b each include a nozzle 210, a channel 212, and at least two open ports 214. The nozzle 210 is configured to convert gas flow from the chamber 204 into a jet stream directed to the channel 212. The channel 212 extends from the nozzle 210, and terminates at a patient side 216. The open ports 214 are akin to the open port 74 (FIG. 2C) described above, and are generally configured to facilitate exhaust of gas during an expiratory phase of operation and entrainment of ambient air (if necessary) during an inspiratory phase.

For example, as shown in FIG. 6B, the first flow circuit 206a includes a first or primary port 214a and a second or secondary port 214b. The primary port 214a is open to the channel 212 at an interior aperture 220 and is open to ambient via an exterior aperture 222 in the generator body 200. The secondary port 214b is similarly open to the channel 212 at an interior aperture 224 and to ambient air via an exterior aperture 226 formed in a tubular body 228 of the channel 212. More particularly, the secondary port exterior aperture 222 is fluidly open to a secondary chamber 230 defined between inner and outer housing sections 232, 234, with the secondary chamber 230, in turn, being open to ambient via a passageway 236 through the generator body 200.

Figure 7:
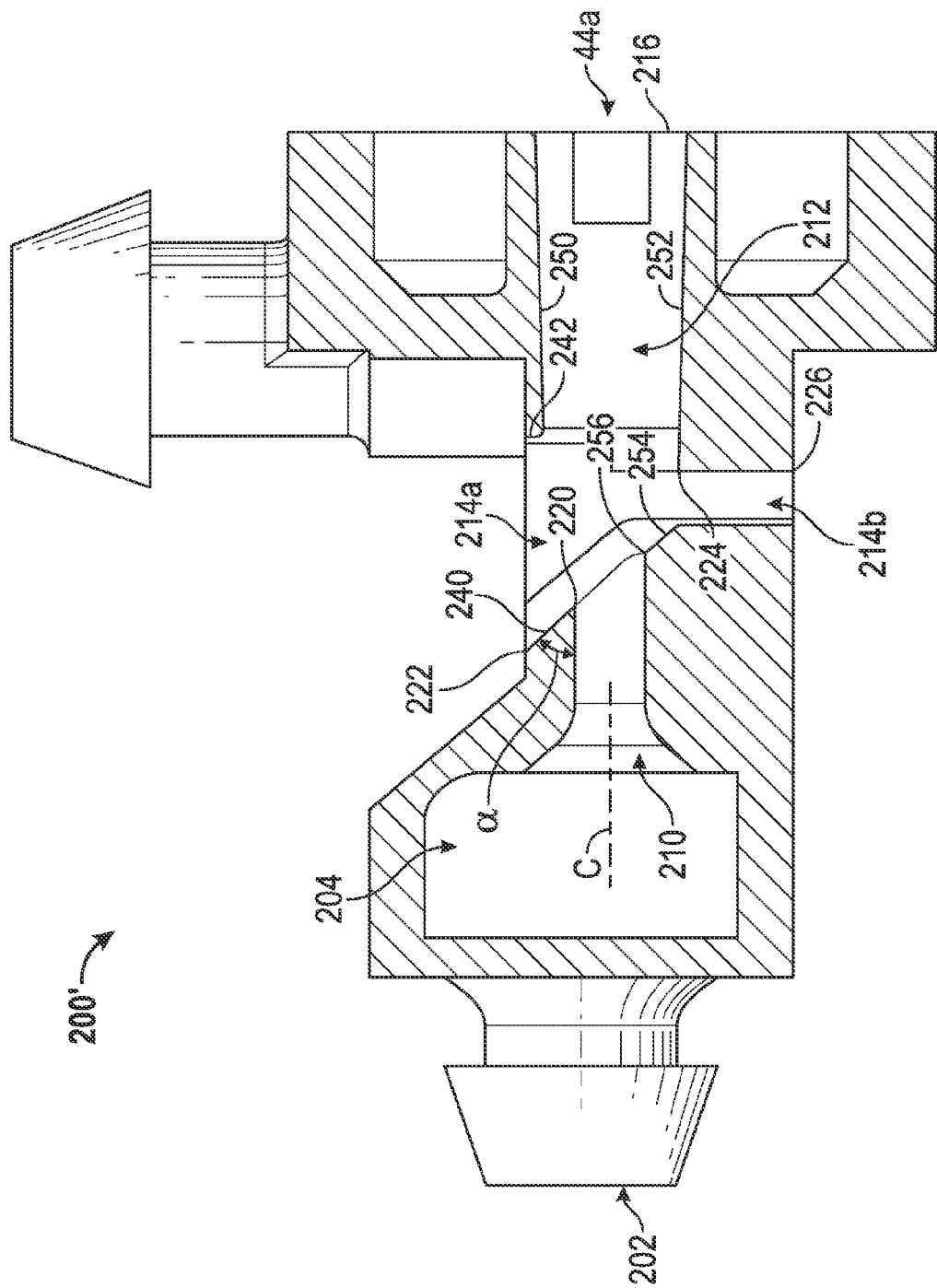
FIG. 7 is a longitudinal cross-sectional view of another generator body in accordance with principles of the present disclosure.

A relationship of the ports 214a, 214b is more clearly evidenced by the cross-sectional view of FIG. 7. As a point of reference, FIG. 7 represents an alternative generator body 200' that is highly akin to the generator body 200 of FIGS. 6A and 6B. With the construction of FIG. 7, however, the gas supply inlet 202 is arranged parallel with the channel 212 (as compared to the more perpendicular arrangement of FIGS. 6A and 6B). Further, the secondary port 214b is shown as being directly open to ambient at the exterior aperture 226 (i.e., the secondary chamber 230 and the passageway 236 of FIG. 6B are omitted), with the secondary port exterior aperture 222 being formed in or at an exterior of the generator body 200'. From a functional standpoint, however, the generator bodies 200, 200' are identical.

The primary port 214a is formed through a thickness of the generator body 200', and is generally defined by a leading end wall 240 and a trailing end wall 242 (relative to the longitudinal cross-sectional view of FIG. 7). As shown, the leading end wall 240 is proximate the nozzle 210 (as compared to the trailing end wall 242), and projects radially outwardly in extension from the channel 212. Stated otherwise, the leading end wall 240 tapers inwardly from the exterior aperture 222 to the interior aperture 220. Thus, relative to a centerline C of the channel 212, extension of the leading end wall 240 defines an included angle α of less than 90°. The trailing end wall 242 can extend between the apertures 220, 222 in a more perpendicular fashion relative to the centerline C. With this construction, the primary port 214a optionally has an expanding cross-sectional area in extension from the channel 212 to the exterior aperture 222 (i.e., a size of the primary port 214a at the interior aperture 220 is less than a size at the exterior aperture 222).

The secondary port 214b extends from the channel 212 at a location generally opposite that of the primary port 214a.

For example, the primary port 214a is located at an upper wall surface 250 of the channel 212, whereas the secondary port 214b is located at a lower wall surface 252. The secondary port 214b can have the generally linear shape shown (in extension from the channel 212), and can be radially aligned with the primary port 214a. For example, the secondary port 214b can be located such that an axis of the secondary port 214b extends through the primary port 214a. In some embodiments, the channel 212 forms a region of increasing diameter between the nozzle 210 and the secondary port 214b. In particular, an angled guide surface 254 can be defined between a nozzle side 256 of the channel 212 and the secondary port interior aperture 224. With this construction, the secondary port 214b, and in particular the secondary port interior aperture 224, is "below" a centerline or axis of the nozzle 210 for reasons made clear below.

The primary port 214a is larger than the secondary port 214b. For example, a cross-sectional area of the primary port 214a at the primary port interior aperture 220 is greater than a cross-sectional area of the secondary port 214b at the secondary port interior aperture 224. Further, a cross-sectional area of the primary port 214a at the primary port exterior aperture 222 is greater than a cross-sectional area of the secondary port exterior aperture 226. Regardless, the primary port 214a facilitates a greater volumetric gas flow as compared to the secondary port 214b.

Figure 8A:
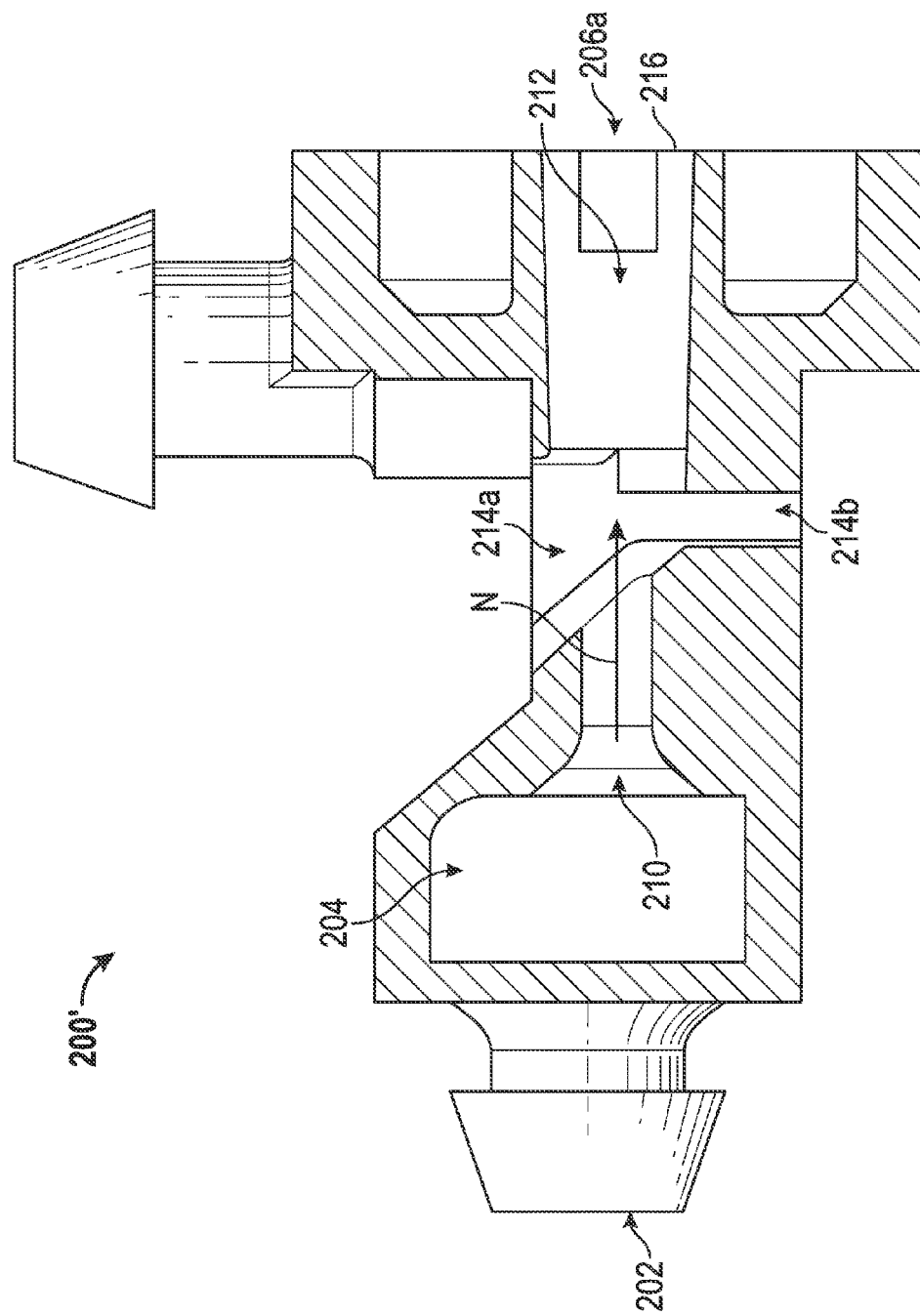
FIG. 8A is a cross-sectional view of the generator body of FIG. 7 and illustrating formation of a jet stream during use.

The open ports 214a, 214b are located in highly close proximity to the nozzle 210. As reflected in FIG. 8A, the flow direction of a jet stream (illustrated by arrow N in FIG. 8A) from the nozzle 210 is generally unaligned with the ports 214a, 214b such that in the absence of other counteractive gas flows or pressures, the jet stream flow N from the nozzle 210 is primarily directed past the ports 214a, 214b and toward the patient side of the channel 212.

Figure 8B:
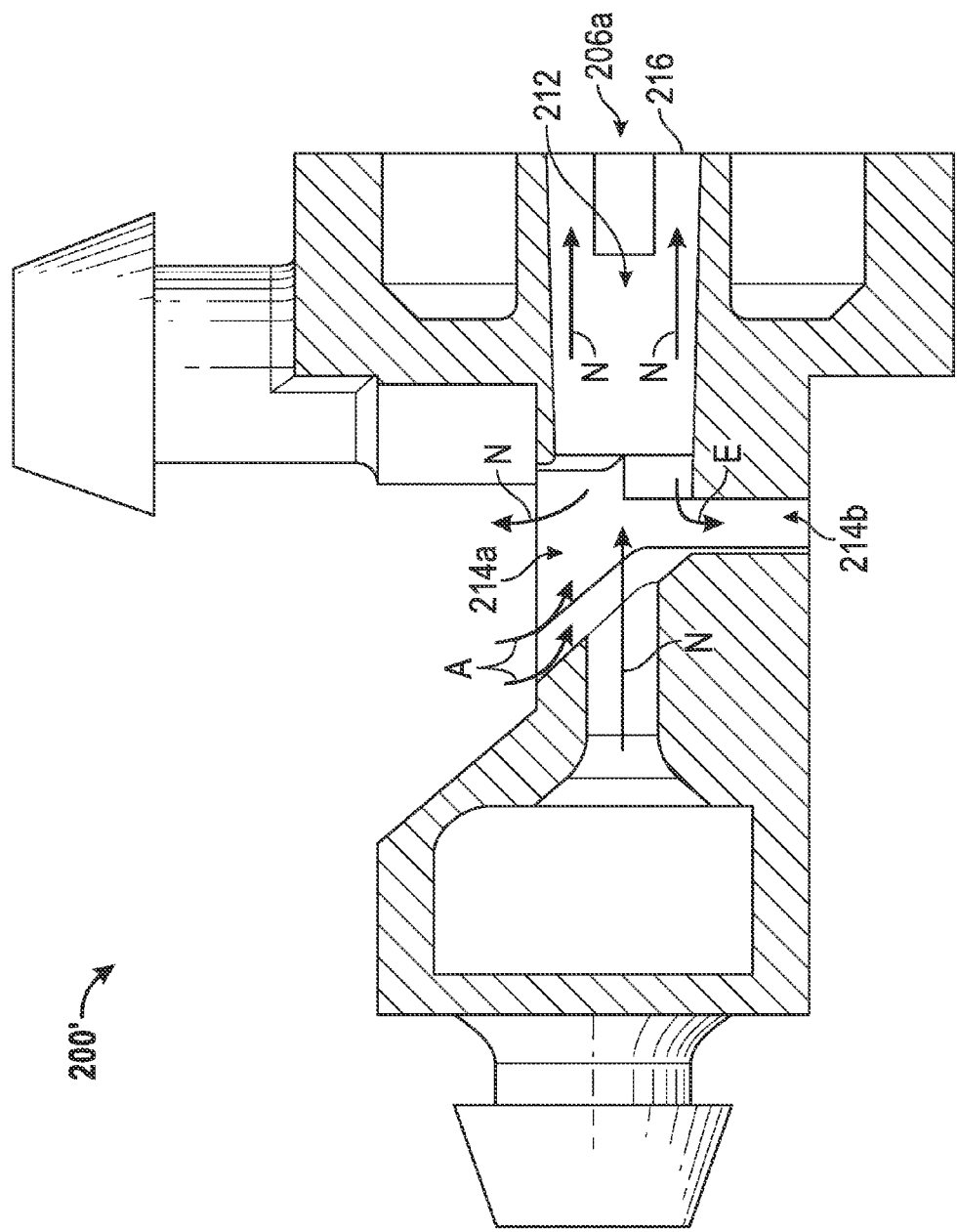
FIG. 8B is a cross-sectional view of the generator body of FIG. 7 and illustrating fluid flow during an inspiratory phase of operation.

During operation, pressurized gas (e.g., from the source of gas 26 (FIG. 1)) is provided to the chamber 204 via the supply inlet 202. The supplied gas is forced into the flow circuits 206. The nozzle 210 of each flow circuit 206 converts the gas flow to the jet stream N that is directed into the corresponding channel 212. During an inspiratory phase of operation (i.e., patient inhaling) reflected in FIG. 8B, at least a portion of the jet stream N passes through the channel 212 and is supplied to the patient via the patient side 216. The jet stream N momentum delivers a continuous positive pressure to the patient side 216. Depending upon the respiratory needs of the patient during inhalation, ambient air is entrained into the delivered flow primarily via the primary port 214a (represented by arrows A in FIG. 8B). Thus, when the patient's inspiratory demand exceeds the set flow rate of the jet stream N, the jet stream N is generated so as to enhance entrainment of supplemental ambient air A for delivery to the patient side 216, and thus the patient. Further, and again depending upon the patient's respiratory needs, excess gas can be exhausted from the channel 212 primarily via the secondary port 214b (identified by arrows E in FIG. 8B). Thus, when the jet stream N flow rate exceeds the inspiratory demand of the patient, excess gas is exhausted via the port(s) 214a, 214b.

Figure 8C:
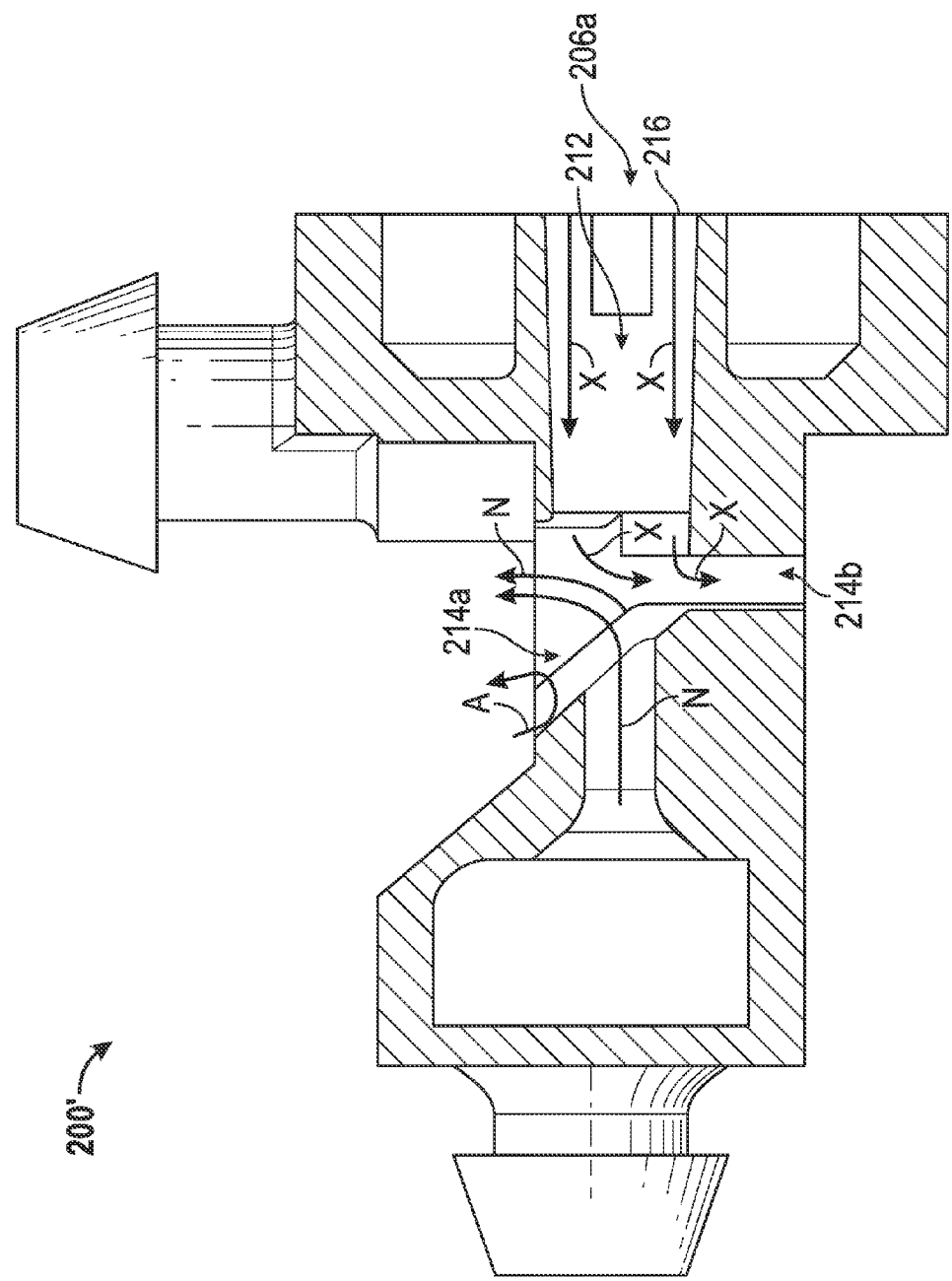
FIG. 8C is a cross-sectional view of the generator body of FIG. 7 and illustrating fluid flow during an expiratory phase of operation.

An expiratory phase of operation (i.e., patient exhaling) is reflected in FIG. 8C. Once again, the gas jet stream N is delivered to the channel 212 at a fixed rate, maintaining the continuous positive airway pressure delivered to the patient by the jet stream's N momentum. Exhaled air (represented by arrows X in FIG. 8C) from the patient is delivered to the channel 212 via the patient side 216 and acts upon the jet stream N (as well as any entrained ambient air A). Because the jet stream N flow has a relatively low momentum, it is easily disrupted by the exhaled air X. Further, the secondary port 214b presents a path of least resistance for the exhaled air X. In particular, the secondary port 214b is located "below" the centerline of the jet stream N so that the exhaled air X is able to more easily flow "under" the jet stream N to the secondary port 214b. Also, the entrained ambient air A at the primary port 214b (in combination with the jet stream N) slightly increases a resistance to flow of the exhaled air X to the primary port 214a. As a result, the exhaled air X flows primarily to the secondary port 214b, with this flow direction causing the jet stream N flow to divert or "turn" toward the primary port 214a. Thus, a significant portion of the jet stream N readily exhausts from the channel 212. The open ports 214a, 214b combine to establish flow patterns that minimize flow resistance to the exhaled air X and thus the corresponding patient's work-of-breathing. The jet stream N, as well as the exhaled air X, readily exhaust from the generator body 200' via the primary and secondary ports 214a, 214b as shown.

Figure 9:
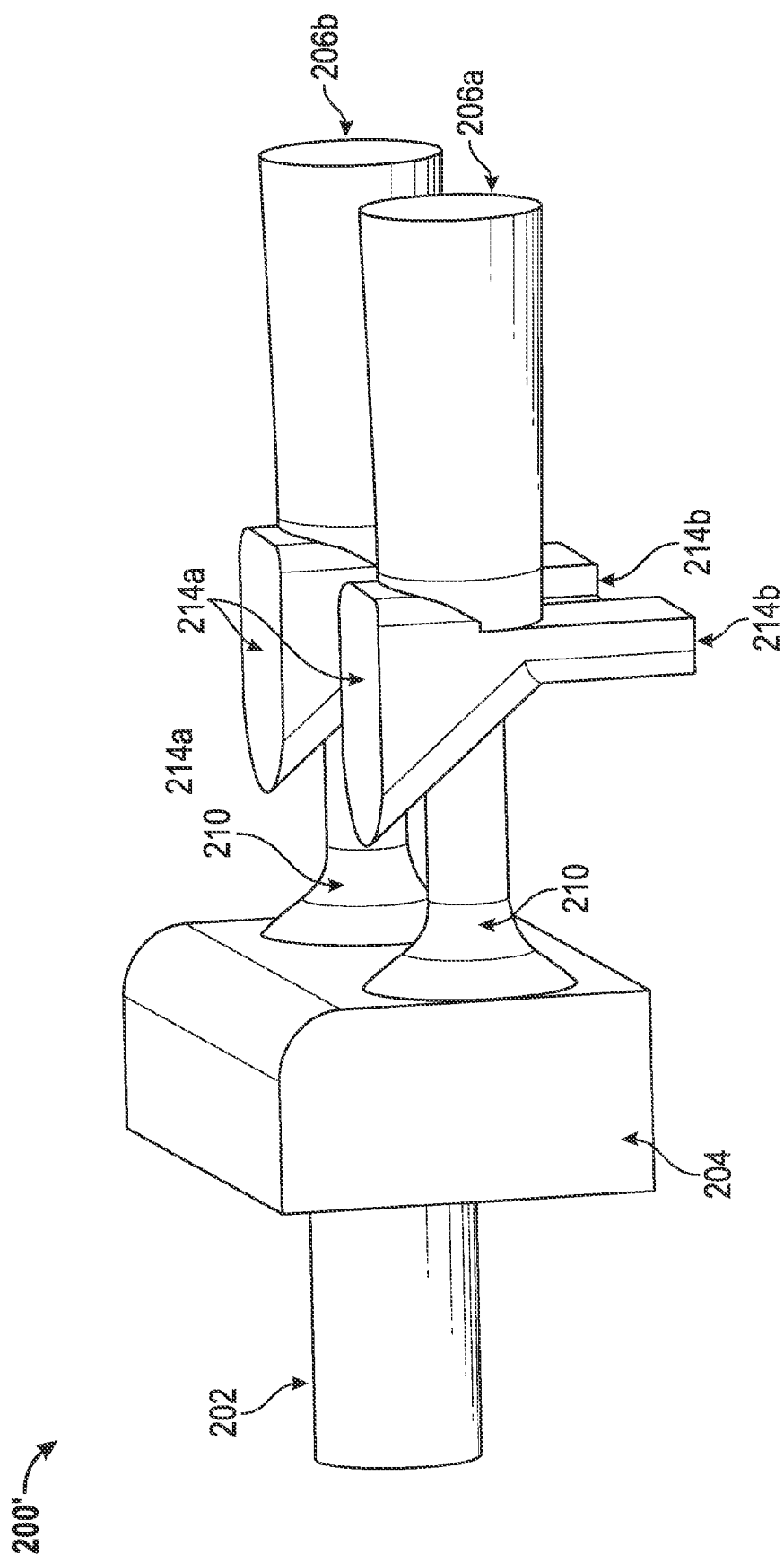
FIG. 9 is a perspective modeling of an internal fluid volume of the generator body of FIG. 7.

Gas flow through the second flow circuit 206b (FIG. 6B) occurs in a virtually identical manner to that described above with respect to the first flow circuit 206a. In this regard, FIG. 9 represents a modeling of an internal or fluid volume of the generator body 200' and reflects the first and second flow circuits 206a, 206b as each having the nozzle 210 fluidly connected to the chamber 204, as well as the primary and secondary ports 214a, 214b facilitating entrainment and exhaust of gas to/from the corresponding channel 212. By combining the relatively large diameter driving jet geometry with the primary and secondary ports 214a, 214b, the generator body 200' can facilitate targeted patient CPAP levels at relatively low supply gas pressures. Further, the secondary exhaust port 214b reduces fluctuation in the delivered CPAP pressure during both inhalation and exhalation such that the work-of-breathing required by a patient is kept very low. These beneficial attributes of the generator body 200' are described in greater detail below.

The generator bodies of the present disclosure have surprisingly been found to beneficially reduce the supplied gas pressure (or "driving pressure") necessary to achieve a targeted CPAP level as compared to conventional designs. For example, FIG. 10 graphically illustrates test results of driving pressure as a function of supplied CPAP for the generator bodies 30 (FIG. 2A), 200' (FIG. 7), as well as two currently available CPAP generator bodies.

In particular, prototype CPAP generators were constructed in accordance with FIGS. 2A and 7, and were subjected to testing by supplying pressurized gas at varying levels to the generator body and recording the resulting level of produced CPAP. Test results for the generator body 30 of FIG. 2A are represented by the plot line 30A in FIG. 10; the test results for the generator body 200' of FIG. 7 are represented by the plot line 200A in FIG. 10. For comparative purposes, an Infant Flow™ CPAP generator (available from CareFusion, Inc.) and an AirLife™ CPAP generator (available from CareFusion, Inc.) were subjected to identical testing. The plot line IF in FIG. 10 represents the test results for the Infant Flow™ generator; the plot line AL reflects the test results for the AirLife™ generator.

Figure 10:
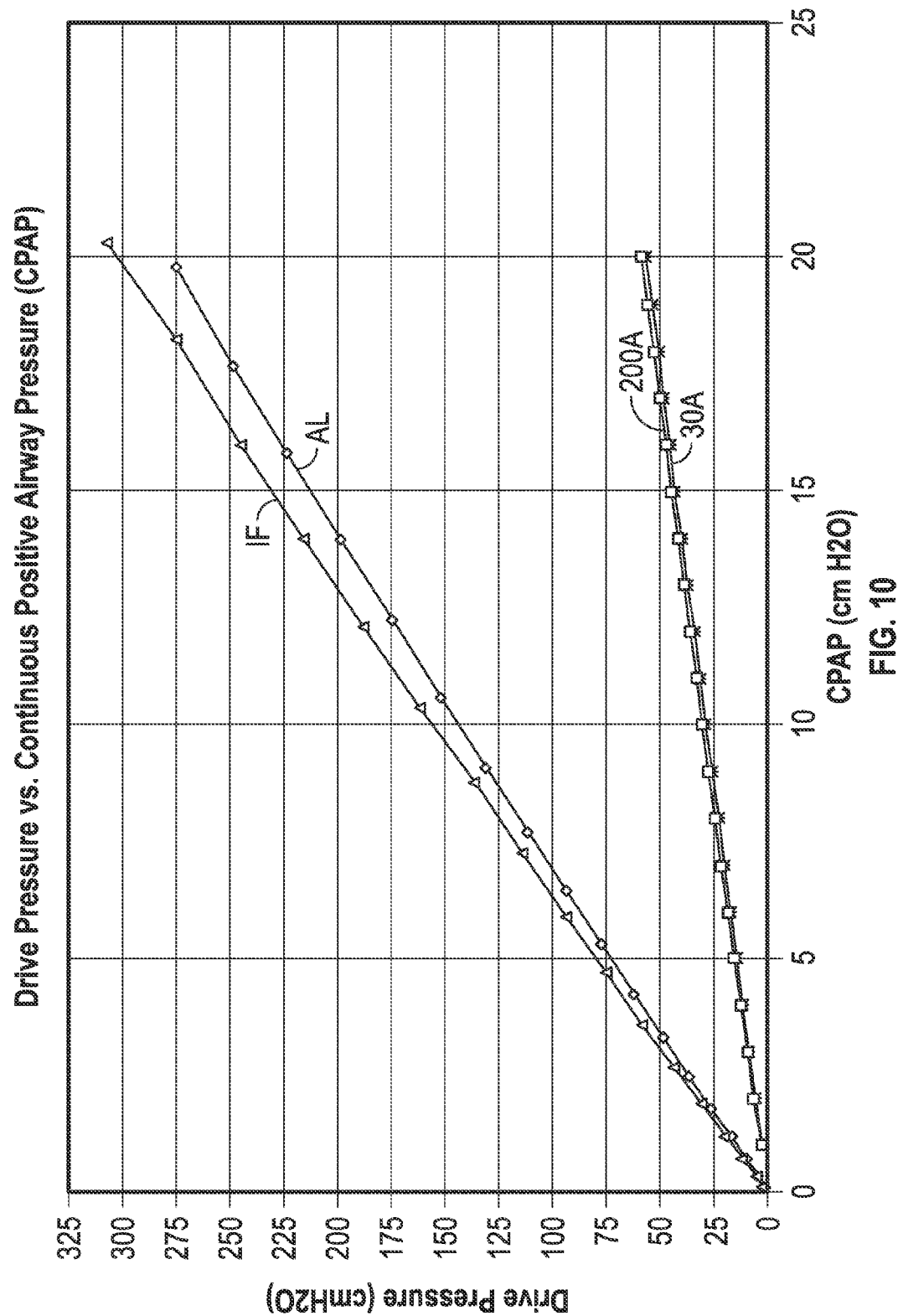
FIG. 10 is a graph of experimental test results comparing driving pressure requirements of generator bodies of the present disclosure with those of currently available nCPAP generator products.

FIG. 10 reveals that a target patient CPAP level can be achieved with the generator bodies of the present disclosure at a driving pressure that is less than those required by existing devices. For example, a target patient CPAP level of 5 cm $H_2O$ may be achieved with a driving pressure not greater than 18 cm $H_2O$ with the generator bodies 30, 200' of the present disclosure; in contrast, existing CPAP generators generally require a driving pressure of greater than 75 cm $H_2O$ to achieve a CPAP level of 5 cm $H_2O$. Similarly, a target patient CPAP level of 20 cm $H_2O$ can be achieved with the generator bodies 30, 200' of the present disclosure with a driving pressure of not greater than 60 cm $H_2O$; by way of comparison, existing CPAP generators generally require a driving pressure of greater than 275 cm $H_2O$ to achieve a CPAP level of 20 cm $H_2O$. With the generator bodies of the present disclosure, then, the reduced driving pressure requirements can provide enhanced safety in that the source of pressurized gas 26 (FIG. 1), that is otherwise in relatively close proximity to the patient during use, operates at a lower pressure as compared to conventional nCPAP systems. In fact, and unlike previous CPAP generators, the generator bodies of the present disclosure are capable of operating within the driving pressure limits of common ventilators, thereby obviating the need for the caregiver to maintain a separate source of pressurized gas (apart from a ventilator that is otherwise normally on-hand) to perform CPAP procedures.

In addition to reducing the necessary driving pressure to achieve target CPAP levels, the generator bodies of the present disclosure have surprisingly been found to reduce the total imposed work-of-breathing (WOB) of the patient. In particular, the flow directing feature (e.g., the ramp regions 110, 112 of FIG. 2C) of the generator body 30 (FIG. 2A) and/or the optimized primary and secondary ambient ports (e.g., the ports 214a, 214b of FIG. 7) associated with the generator bodies 200 (FIG. 6A), 200' (FIG. 7) enable the CPAP-generating jet stream to optimally self-adjust thereby keeping pressure fluctuations beneficially low (as compared to currently available CPAP generators) in turn lowering the total imposed WOB.

Figure 11:
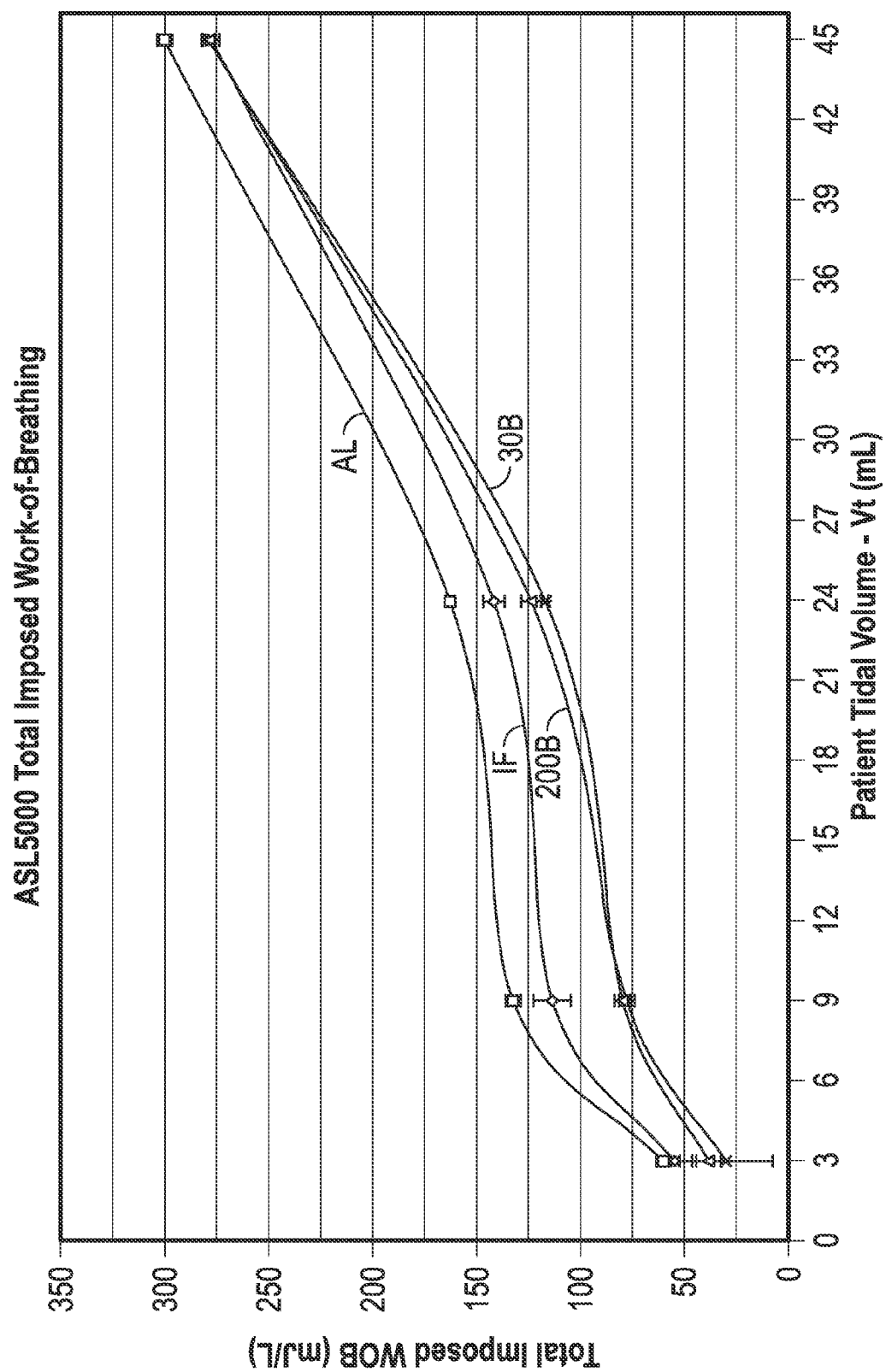
FIG. 11 is a graph of experimental test results comparing the total imposed work-of-breathing requirements of the generator bodies of the present disclosure with those of currently available nCPAP generator products.

Total imposed WOB testing was performed on the prototype generator bodies 30, 200', the Infant Flow™ generator, and the AirLife™ generator samples used with the driving pressure tests described above by connecting the samples to an industry-accepted lung simulator (IngMar Medical ASL 5000 Breathing Simulator utilizing Software Version 2.2.22a and available from IngMar Medical, Ltd., of Pittsburgh, Pa.). Total imposed WOB was measured and recorded at several simulated patient tidal volumes for each generator at a CPAP setting of 5 cm $H_2O$. The total imposed WOB test results are shown in FIG. 11. The results for the generator body 30 are plotted by the line 30B in FIG. 11; the test results for the generator body 200' are plotted by the line 200B. By way of comparison, the total imposed WOB test results for the available Infant Flow™ CPAP generator are plotted by the line IF, whereas the test results for the available AirLife™ CPAP generator are plotted by the line AL. As shown, the total imposed WOB for a 9 mL patient tidal volume is not greater than 80 mJ/L using the generator bodies of the present disclosure. In contrast, the total imposed WOB for a 9 mL patient tidal volume is greater than 115 mJ/L with currently available CPAP generators (that otherwise require the comparatively higher driving pressures as described above). Similarly, the total imposed WOB for a 24 mL patient tidal volume is not greater than 130 mJ/L with the generator bodies of the present disclosure; in contrast, the total imposed WOB requirements at a 24 mL patient tidal volume is greater than 140 mJ/L with currently available CPAP generators (that require comparatively higher driving pressures). As used throughout this specification, a total imposed WOB parameter of a generator body is determined by testing with the above-identified IngMar Medical ASL 5000 Breathing Simulator.

The CPAP devices, and related systems and methods, of the present disclosure provide a marked improvement over previous designs. In particular, the generator bodies envisioned by the present disclosure have reduced driving pressure requirements necessary for delivering desired levels of CPAP, as well as reduced total imposed WOB properties. Further, by incorporating low profile ports and condensed jet stream features, the generator bodies of the present disclosure can be relatively small as compared to existing designs.

Although the present disclosure has been described with reference to preferred embodiments, workers skilled in the art will recognize that changes can be made in form and detail without departing from the spirit and scope of the present disclosure.

What is claimed is:

1. A nasal continuous positive airway pressure device for use in a CPAP system to assist patient breathing, the device comprising:
   a generator body forming:
      an inlet for fluid connection to a source of pressurized gas,
      a chamber fluidly connected to the inlet,
      first and second flow circuits fluidly connected to the chamber, each of the flow circuits including:
         a nozzle defining an inlet end and an outlet end, the inlet end fluidly connected to the chamber and the outlet end having a diameter less than a diameter of the inlet end,
         a channel defining:
            a nozzle side fluidly connected to the outlet end of the nozzle,
            a patient side opposite the nozzle side for directing gas to and from a patient's naris,
            a first ramp region between the nozzle and patient sides, the first ramp region tapering in diameter toward the patient side,
            a second ramp region between the first ramp region and the patient side, the second ramp region expanding in diameter toward the patient side, and
            an open port fluidly connected to the channel at a location between the nozzle side and the patient side, the open port angularly aligned above the first ramp region,
         wherein the nozzle is configured to create a jet stream from pressurized gas in the chamber, the jet stream being deliverable to the channel and divertible to the open port, and
      a patient interface piece fluidly connected to the patient side of the channels.

2. The device of claim 1, wherein in longitudinal cross-section, the channel of each of the flow circuits is defined by a lower wall surface opposite an upper wall surface, the corresponding open port being formed in the upper wall surface, and further wherein the ramp regions are defined along the lower wall surface including the first ramp region extending to a transition location between the open port and the corresponding patient side and the second ramp region extending from the transition location toward the patient side, and further wherein the lower wall surface is non-parallel with the upper wall surface along at least the second ramp region.

3. The device of claim 2, wherein the lower wall surface projects toward the upper wall surface in extension to the transition location along the first ramp region, and the lower wall surface projects away from the upper wall surface in extension from the transition location toward the patient side along the second ramp region.

4. The device of claim 3, wherein a slope of the first ramp region is less than a slope of the second ramp region.

5. The device of claim 2, wherein relative to a direction from the nozzle side toward the patient side, the lower wall surface is inclined along the first ramp region and declined along the second ramp region.

6. The device of claim 2, wherein the second ramp region is configured to direct exhaled airflow from the patient side upwardly toward the jet stream.

7. The device of claim 1, wherein the generator body is configured to establish: an inspiratory flow pattern during an inspiratory stage of breathing, the inspiratory flow pattern including gas flow from the chamber, along each of the circuits, and to the patient side of each of the channels; and an expiratory flow pattern during an expiratory stage of breathing, the expiratory flow pattern including gas flow from the patient side of each of the channels and to the corresponding open port, including diversion of the jet stream to the corresponding open port.

8. The device of claim 7, wherein the expiratory flow pattern further includes gas flow from the patient side being deflected toward the open port by the second ramp region.

9. The device of claim 8, wherein gas flow directed toward the open port as part of the expiratory flow pattern diverts the jet stream to the open port.

10. The device of claim 1, wherein the generator body is configured to establish a continuous positive airway pressure level of 20 cm $H_2O$ at a driving pressure of gas delivered to the inlet of not greater than 110 cm $H_2O$.

11. The device of claim 10, wherein the continuous positive airway pressure level of 20 cm $H_2O$ is established by the generator body at a driving pressure of not greater than 60 cm $H_2O$.

12. The device of claim 1, wherein the generator body is configured to establish a continuous positive airway pressure level of 5 cm $H_2O$ at a driving pressure of gas delivered to the inlet of not greater than 25 cm $H_2O$.

13. The device of claim 12, wherein the continuous positive airway pressure level of 5 cm $H_2O$ is established by the generator body at a driving pressure of not greater than 18 cm $H_2O$.

14. The device of claim 1, wherein the generator body is configured to establish a continuous positive airway pressure level of 5 cm $H_2O$ and a total imposed work-of-breathing of not greater than 140 mJ/L at a driving pressure of gas delivered to the inlet of not greater than 25 cm $H_2O$ for a 9 mL tidal volume patient.

15. The device of claim 14, wherein the driving pressure is not greater than 18 cm $H_2O$.

16. The device of claim 14, wherein the total imposed work-of-breathing is not greater than 80 mJ/L for a 9 mL tidal volume patient.

17. The device of claim 1, wherein the generator body is configured to establish a continuous positive airway pressure level of 5 cm $H_2O$ and a total imposed work-of-breathing of not greater than 200 mJ/L at a driving pressure of gas delivered to the inlet of not greater than 25 cm $H_2O$ for a 24 mL tidal volume patient.

18. The device of claim 17, wherein the driving pressure is not greater than 18 cm $H_2O$.

19. The device of claim 17, wherein the total imposed work-of-breathing is not greater than 130 mJ/L for a 24 mL tidal volume patient.

20. The device of claim 1, wherein a ratio of a height of the channel at the patient side to the diameter of the nozzle at the outlet end is in the range of 2.29-2.50.

21. The device of claim 1, wherein the diameter of the nozzle at the outlet end is in the range of 0.04-0.07 inch.

22. A nasal continuous positive airway pressure system for assisting patient breathing, the system comprising:
   a generator body forming:

an inlet,
a chamber fluidly connected to the inlet,
first and second flow circuits fluidly connected to the chamber, each of the flow circuits including:
 a nozzle defining an inlet end and an outlet end, the inlet end fluidly connected to the chamber and the outlet end having a diameter less than a diameter of the inlet end,
 a channel having:
  a nozzle side fluidly connected to the outlet end of the nozzle,
  a patient side opposite the nozzle side,
  a first ramp region between the nozzle and patient sides, the first ramp region tapering in diameter toward the patient side,
  a second ramp region between the first ramp region and the patient side, the second ramp region expanding in diameter toward the patient side, and
  an open port fluidly connected to the channel at a location between the nozzle side and the patient side, the open port angularly aligned above the first ramp region;
a patient interface piece fluidly connected to the patient side of the channels; and
a source of pressurized gas fluidly connected to the inlet;
wherein upon securement of the patient interface piece to a patient's nares, the system is configured to generate a continuous positive airway pressure in the patient by delivering gas from the source of pressurized gas to the nozzles that in turn emits a gas jet stream within the corresponding channel in a direction of the patient interface piece.

23. The system of claim 22, wherein in longitudinal cross-section, the channel of each of the flow circuits is defined by a lower wall surface opposite an upper wall surface, the corresponding open port being formed in the upper wall surface, and further wherein the ramp regions are defined along the lower wall surface including the first ramp region extending to a transition location between the open port and the corresponding patient side and the second ramp region extending from the transition location toward the patient side, and further wherein the lower wall surface is non-parallel with the upper wall surface along at least the second ramp region.

24. The system of claim 23, wherein the lower wall surface projects toward the upper wall surface in extension to the transition location along the first ramp region, and the lower wall surface projects away from the upper wall surface in extension from the transition location toward the patient side along the second ramp region.

25. The system of claim 24, wherein a slope of the first ramp region is less than a slope of the second ramp region.

26. The system of claim 23, wherein relative to a direction from the nozzle side toward the patient side, the lower wall surface is inclined along the first ramp region and declined along the second ramp region.

27. The system of claim 23, wherein the second ramp region is configured to direct exhaled airflow from the patient side upwardly toward the jet stream.

28. The system of claim 22, wherein the generator body is configured to establish a continuous positive airway pressure level of 20 cm $H_2O$ at a driving pressure of gas delivered to the inlet of not greater than 110 cm $H_2O$.

29. The system of claim 28, wherein the continuous positive airway pressure level of 20 cm $H_2O$ is established by the generator body at a driving pressure of not greater than 60 cm $H_2O$.

30. The system of claim 22, wherein the system is configured to establish a continuous positive airway pressure level of 5 cm $H_2O$ and a total imposed work-of-breathing of not greater than 140 mJ/L at a driving pressure of gas delivered from the source of pressurized gas to the inlet of not greater than 25 cm $H_2O$ for a 9 mL tidal volume patient.

31. The system of claim 30, wherein the driving pressure is not greater than 18 cm $H_2O$.

32. The system of claim 30, wherein the total imposed work-of-breathing is not greater than 80 mJ/L for a 9 mL tidal volume patient.

33. The system of claim 22, wherein the generator body is configured to establish a continuous positive airway pressure level of 5 cm $H_2O$ and a total imposed work-of-breathing of not greater than 200 mJ/L at a driving pressure of gas delivered to the inlet of not greater than 25 cm $H_2O$ for a 24 mL tidal volume patient.

34. The system of claim 33, wherein the driving pressure is not greater than 18 cm $H_2O$.

35. The system of claim 33, wherein the total imposed work-of-breathing is not greater than 130 mJ/L for a 24 mL tidal volume patient.

36. The system of claim 22, wherein the source of pressurized gas is a ventilator.

* * * * *